United States Patent
Santamore et al.

(10) Patent No.: US 8,452,419 B2
(45) Date of Patent: May 28, 2013

(54) CARDIAC RHYTHM MANAGEMENT SYSTEM WITH INTRAMURAL MYOCARDIAL PACING LEADS AND ELECTRODES

(75) Inventors: William P. Santamore, Medford, NJ (US); Jeanne M. Lesniak, Natick, MA (US)

(73) Assignee: Cormend Technologies, LLC, Wilmington, DE (US)

( * ) Notice: Subject to any disclaimer, the term of this patent is extended or adjusted under 35 U.S.C. 154(b) by 0 days.

(21) Appl. No.: 12/834,377

(22) Filed: Jul. 12, 2010

(65) Prior Publication Data

US 2010/0280565 A1 Nov. 4, 2010

Related U.S. Application Data

(60) Division of application No. 11/831,643, filed on Jul. 31, 2007, now abandoned, which is a continuation of application No. 10/626,602, filed on Jul. 25, 2003, now abandoned.

(60) Provisional application No. 60/398,586, filed on Jul. 26, 2002.

(51) Int. Cl.
*A61N 1/05* (2006.01)
(52) U.S. Cl.
USPC ............... 607/122; 607/5; 607/9; 607/116; 607/119; 607/125; 607/126; 607/132

(58) Field of Classification Search
USPC ............... 607/122, 125, 126, 5, 9, 116, 119, 607/132
See application file for complete search history.

(56) References Cited

U.S. PATENT DOCUMENTS

| | | | | |
|---|---|---|---|---|
| 5,305,745 A | * | 4/1994 | Zacouto | 600/324 |
| 5,489,294 A | * | 2/1996 | McVenes et al. | 607/120 |
| 5,871,528 A | * | 2/1999 | Camps et al. | 607/119 |
| 6,296,630 B1 | * | 10/2001 | Altman et al. | 604/508 |
| RE37,463 E | * | 12/2001 | Altman | 600/374 |
| 6,332,863 B1 | * | 12/2001 | Schweich et al. | 600/16 |
| 6,343,605 B1 | * | 2/2002 | Lafontaine | 128/898 |
| 7,311,731 B2 | * | 12/2007 | Lesniak et al. | 623/3.1 |
| 7,988,727 B2 | * | 8/2011 | Santamore et al. | 623/2.42 |
| 8,145,304 B2 | * | 3/2012 | Moffitt et al. | 607/9 |
| 2002/0188170 A1 | * | 12/2002 | Santamore et al. | 600/37 |
| 2003/0105493 A1 | * | 6/2003 | Salo | 607/9 |
| 2005/0080402 A1 | * | 4/2005 | Santamore et al. | 606/1 |
| 2005/0271631 A1 | * | 12/2005 | Lee et al. | 424/93.7 |
| 2008/0069801 A1 | * | 3/2008 | Lee et al. | 424/93.1 |
| 2010/0168651 A1 | * | 7/2010 | Kassab et al. | 604/28 |
| 2010/0305634 A1 | * | 12/2010 | Moffitt et al. | 607/5 |

\* cited by examiner

*Primary Examiner* — Niketa Patel
*Assistant Examiner* — Christopher A Flory
(74) *Attorney, Agent, or Firm* — Novak Druce Connolly Bove + Quigg LLP

(57) ABSTRACT

Medical devices and therapeutic methods for use in the field of cardiology, cardiac rhythm management and interventional cardiology, and more specifically to catheter-based systems for implantation of pacing leads and electrodes, or intramural myocardial reinforcement devices, within the myocardial wall of the heart, such as the ventricles, to provide improved cardiac function.

24 Claims, 13 Drawing Sheets

CARDIAC RHYTHM MANAGEMENT SYSTEM WITH INTRAMURAL MYOCARDIAL PACING LEADS AND ELECTRODES

This application claims the benefit of and priority to U.S. patent application Ser. No. 11/831,643, pending, filed Jul. 31, 2007, which claims the benefit of priority to U.S. patent application Ser. No. 10/626,602, abandoned, filed Jul. 25, 2003, which claims the benefit of priority to U.S. Provisional Application No. 60/398,586 filed Jul. 26, 2002, the contents of all of which are incorporated herein in their entirety.

FIELD OF THE INVENTION

The invention relates generally to medical devices and therapeutic methods for their use in the field of cardiology, cardiac rhythm management and interventional cardiology, and more specifically to catheter-based systems for implantation of pacing leads and electrodes, or intramural myocardial reinforcement devices, within the myocardial wall of the heart, such as the ventricles, to provide improved cardiac function.

BACKGROUND OF THE INVENTION

In the normal heart, the electrical activity, which initiates the subsequent mechanical contraction, is very organized. In general, once one cell is activated, the adjacent cells of the heart will become activated to propagate the electrochemical depolarization associated with systolic contraction of the heart muscle. Unlike skeletal muscle, each heart muscle is electrically connected to its neighbors. This activation usually starts in the right atrium, in the sinoatrial node. From here, the electrical activity spreads across the right and left atrium through either special conduction (i.e., faster pathways) or through normal atrial tissue. To electrically activate the main pumping chambers of the heart, the left and right ventricles, the electrical activity passes through the atrioventricular node. Within this node, the spread of electrical activity is relatively slow. Mechanically, this allows the atrium to contract and pump blood into the ventricles before the ventricles contract.

Following this relatively slow spread of cardiac action potential, the electrical activation travels rapidly down a special conduction pathway, known as the bundle of His. The bundle of His divides into right and left bundle branches; the left dividing in turn into an anterior and posterior branch. This network consists of high-speed conduction fibers, known as the Purkinje fibers. From here, the remaining ventricular muscle cells are activated. This high-speed network is essential for a synchronized contraction of each ventricle relative to associated atria, and for efficient, mechanical synchrony between the left and right ventricles.

Ischemic heart disease and other clinical problems (fibrosis, etc.) can cause conduction delays and/or blockage in this high-speed network. For example, a left bundle branch block leads to late electrical activation of the left ventricular free wall. These conduction problems change the QRS complex in the ECG to a wide QRS complex greater than 120 ms. The corresponding electrical conduction delays cause mechanical dysfunction, decreased cardiac output, as well as valvular regurgitation. Clinical studies have shown early septal circumferential shortening, followed by late stretch as the left ventricular free wall shortenings begins (Kawaguchi M, Murabayashi T, Fetics B J, Nelson G S, Sarmejima H, Nevo E, Kass D A. Quantitation of basal dyssynchrony and acute resynchronization from left or biventricular pacing by novel-contrast variability imaging. Journal of the American College of Cardiology 2002; 39:2052-8). This electrical-mechanical dyssynchrony decreases cardiac output and may cause or exacerbate mitral regurgitation.

The electrical synchrony can be partially restored by biventricular pacing. A pacemaker is implanted in the patient along with a right atrial, right ventricular, and left ventricular lead. The right atrial lead is used to sense the electrical activity in the right atrium and/or to stimulate the right atrium. The pacemaker senses this electrical activity and after a programmable delay (i.e., the delay can be different for each ventricle) electrically stimulates the right and left ventricles, thereby re-establishing electrical synchrony. The leads can be either bipolar or unipolar, and general consist of a coiled conductor, which is electrically isolated from the surrounding tissue. Numerous materials, such as platinum or tantalum coated MP35N alloy wire, can be used for the conductor. At the distal end, the conductor makes electrical contact with the tissue via an electrode, commonly a ring electrode. The electrode can elude an anti-inflammatory cortico-steroid, such as sodium dexamethasone, to reduce irritation of tissue adjacent to the electrode. Insulation materials such as polyurethane, silicone, and ethylene tetrafluor ethylenefluoropolymer are used. The proximal end is directly connected to the pacemaker through an IS-1 standard connector with a sealing-ring (de Voogt W G, Pacemaker leads: Performance and progress. American Journal of Cardiology 1999; 83:187 D-191D).

Initial clinical trials show that resynchronizaton therapy increases exercise capacity and peak oxygen consumption, increases left ventricular ejection fraction, and decreases left ventricular end-diastolic size: all very positive changes for patients with heart failure. These studies also indicate that left ventricular pacing may be as effective as biventricular pacing (Abraham W T, Fisher W G, Smith A L, Delurgio D B, Leon A R, Loh E, Kocovic D Z, packer M, Clavell A L, Hayes D L, Ellestad M, Messenger J. Cardiac resynchronization in chronic heart failure. New England Journal of Medicine 2002; 346:1845-53).

A major technical and clinical challenge associated with these applications concerns the issue of how to place a left ventricular free wall electrode. A typical location for this left ventricular lead is the lateral left ventricular free wall mid way between the base and apex (Auicchio A, Klein H, Tockman B, Sack S, Stellbrink C, Neuzner J, Kramer A, Ding J, Pochet T, Maarse A, Spinelli J. Transvenous biventricular pacing for heart failure: can the obstacles be overcome? American Journal of Cardiology 1999; 83:136 D-142D.). A specialized left ventricular lead is placed into a distal cardiac vein by way of the coronary sinus through a guiding catheter. For example, the EASYTRACK system (Guidant, Si Paul, Minn.) is a transvenous, coronary venous, unipolar pace/sense lead for left ventricular stimulation. [Purerfellner H, Nesser H J, Winter S. Schwierz T, Hornell H, Maertens S. Transvenous left ventricular lead implantation with the EASYTRACK lead system: The European experience. Am J Cardiol 2000; 86 (suppl):157K-164K.] The lead is delivered through a guiding catheter with a specific design to facilitate access to the ostium of the coronary sinus. This catheter provides pushability by incorporating an internal braided-wire design. The distal end of the catheter features a soft tip to prevent damaging of the right atrium or the coronary sinus. The EASYTRACK lead has a 6 Fr. outer diameter and an open-lumen inner conductor coil that tracks over a standard 0.014-inch percutaneous transluminal coronary angioplasty guidewire. The distal end of the electrode consists of a flexible silicone rubber tip designed to be atraumatic to vessels during lead advancement.

In many patients (i.e., at least 10%), either the lead cannot be placed or complications (e.g., dissection or perforation of the coronary sinus or cardiac vein, complete heart block, hemopericardium, and cardiac arrest) occur (Abraham 2002). Because of these difficulties, the left ventricular lead is sometimes placed through a small thoracotomy (Auricchio A, Stellbrink C, Sack S, Block M, Vogt J, Bakker P, Huth C, Schondube F, Wolfhard U, Bocker D, Krahnefeld O, Kirkels H. Long-term clinical effect of hemodynamically optimized cardiac resynchronization therapy in patients with heart failure and ventricular conduction delay. Journal of the American College of Cardiology 2002; 39:2026-33.).

SUMMARY OF THE INVENTION

In accordance with the present invention, devices and methods are provided for an effective intervention, which contemplates the implantation of intramural, myocardial pacing leads and electrodes, as well as implants for localized reinforcement of infarcted myocardial tissue, by delivery from the right ventricle directly into the left ventricular free wall.

The accompanying drawings, which are incorporated in and constitute a part of this specification, illustrate one (several) embodiment(s) of the invention, and together with the specification serve to explain the principles of the invention.

DESCRIPTION OF ILLUSTRATIVE EMBODIMENTS

Reference will now be made in detail to exemplary embodiments of the invention, examples of which are illustrated in the accompanying drawings. Wherever possible, the same reference numbers will be used throughout the drawings to refer to the same or like parts.

Introduction and placement of appropriate ventricular pacing leads and electrodes are the subject of this application, as well as improved methods for introducing myocardial tissue reinforcement devices within the intramural space. It is believed that several problems associated with traditional introduction and placement of left ventricular pacing leads can be circumvented according to the present invention, which provides for placement of the lead directly into the intramural space of the left ventricular myocardium via right ventricular catheter introduction.

Figure 1A:
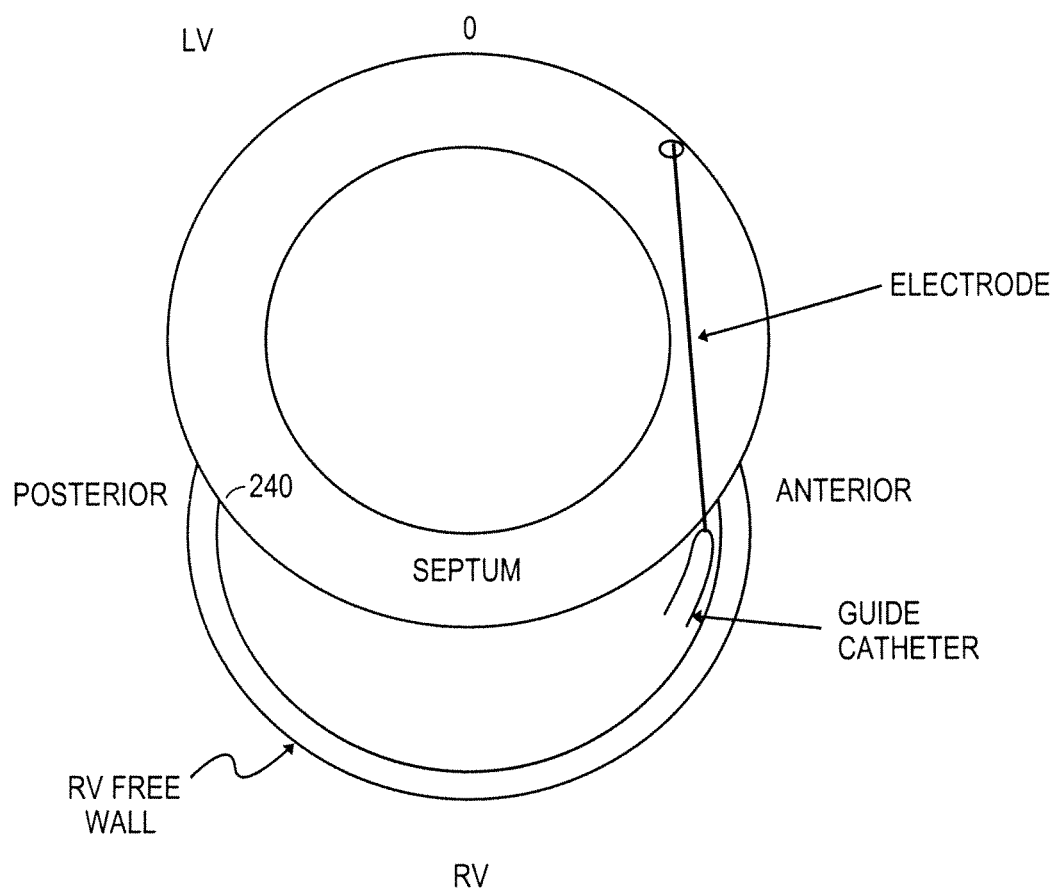
FIG. 1a is a cross-sectional, planar view of the left and right ventricles with the distal end of a guide catheter wedged into the junction of the right ventricular free wall and the interventricular septum, to facilitate introduction and implanting of a pacing lead within the intramural myocardial tissue of the heart.

FIG. 1 depicts a cross-sectional, planar, short-axis view of the left and right ventricles. Using a novel technique, a guide catheter is first introduced via a vein (e.g., right external jugular vein) and advanced into the right ventricle. The distal end of the guide catheter is wedged into the junction of the right ventricular free wall and the interventricular septum. X-ray or echo-based imaging facilitates this catheter positioning. In this example, the guide catheter is placed by the anterior surface, but the guide catheter can also be placed by the posterior surface. A straight pacing lead is pushed from the guide catheter directly into the intramural tissues of the myocardium. The pacing lead and electrode system is advanced well into the left ventricular free wall comprising the intramural tissues. In this example, an imaginary position designated in FIG. 1, indicated at a 0 degree position, representing the ideal ventricular lead placement. The right ventricular free walls intercept the left ventricle at approximately 120 and 240 degrees. It is understood that most straight pacing leads are capable of reaching locations approximately 30 degrees away from the 0 degree position. In many patients, the conduction delays are not symmetrical between the anterior and posterior wall. If the posterior wall were activated first, then the pacing lead position, as depicted in FIG. 1a, is ideal.

Figure 1B:
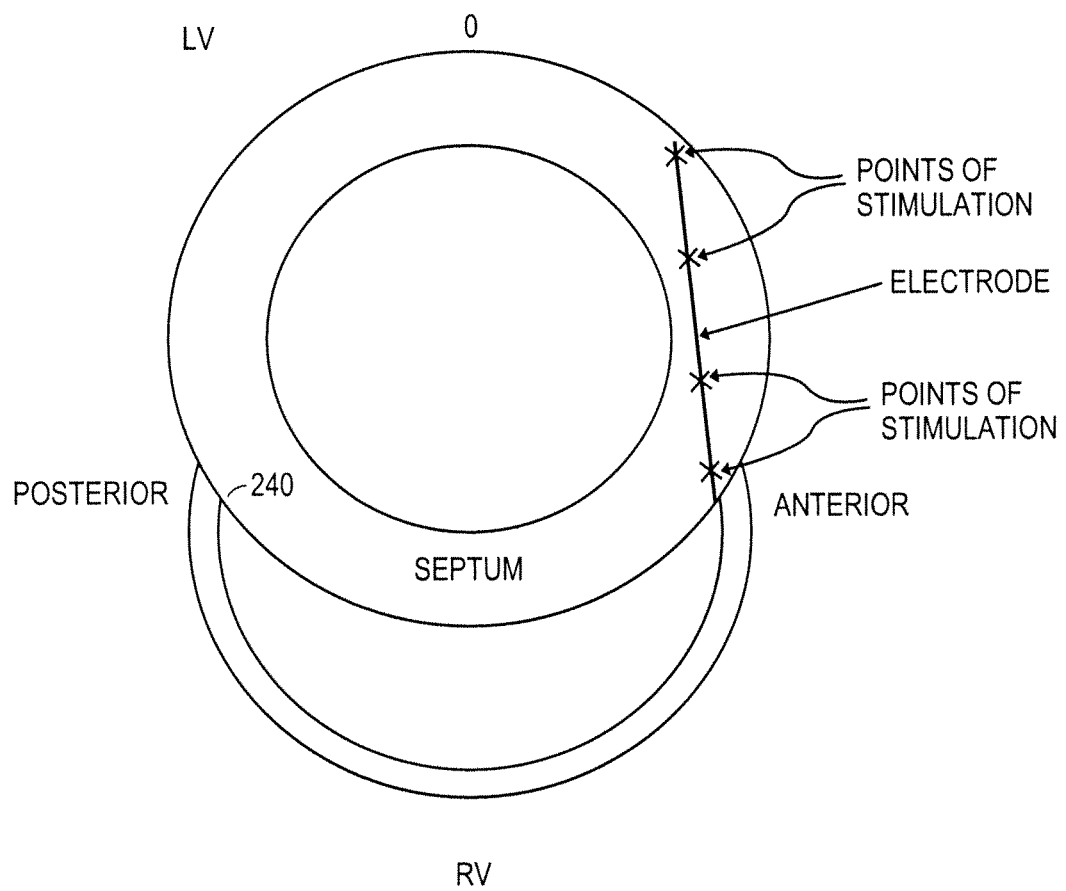
FIG. 1b depicts an intramural pacing lead with multiple electrode sites for pacing.

FIG. 1b illustrates an exemplary pacing lead providing multiple sites for intramural pacing. In between these pacing spots, the lead is electrically isolated for the myocardium. At the pacing sites, the lead can be provided with appropriately spaced-apart electrodes along its distal shaft which establish a direct electrical contact with the myocardium at desired locations. All the sites or selected sites can be used to re-establish electrical synchrony.

Figure 1C:
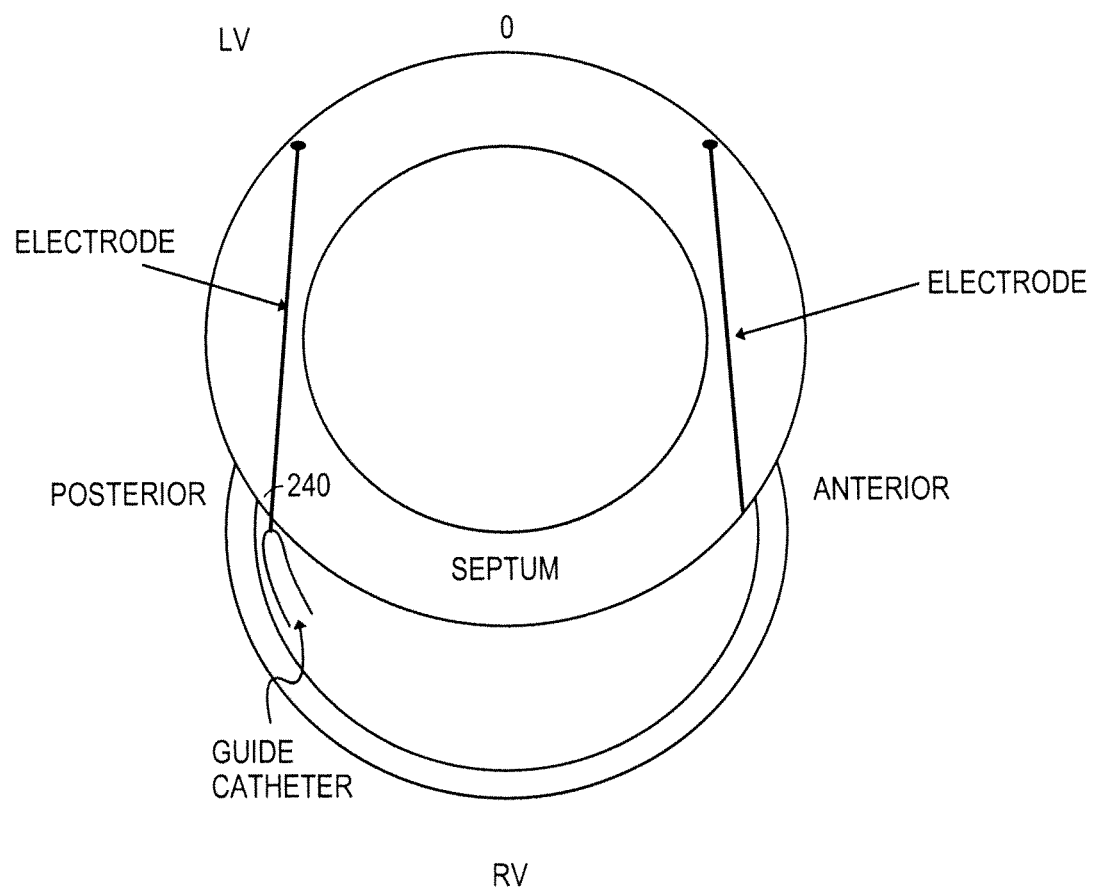
FIG. 1c illustrates multiple, intramural pacing leads implanted within the left ventricular myocardium.

FIG. 1c illustrates an exemplary anterior pacing lead within the myocardium. The guide catheter has been removed, and the lead has been connected to the stimulator. A second pacing lead can be similarly placed. The guide catheter is repositioned by the posterior junction of the septum and the right ventricular free wall. A straight pacing lead is advanced from the guide catheter into the posterior left ventricular free wall.

Figure 2:
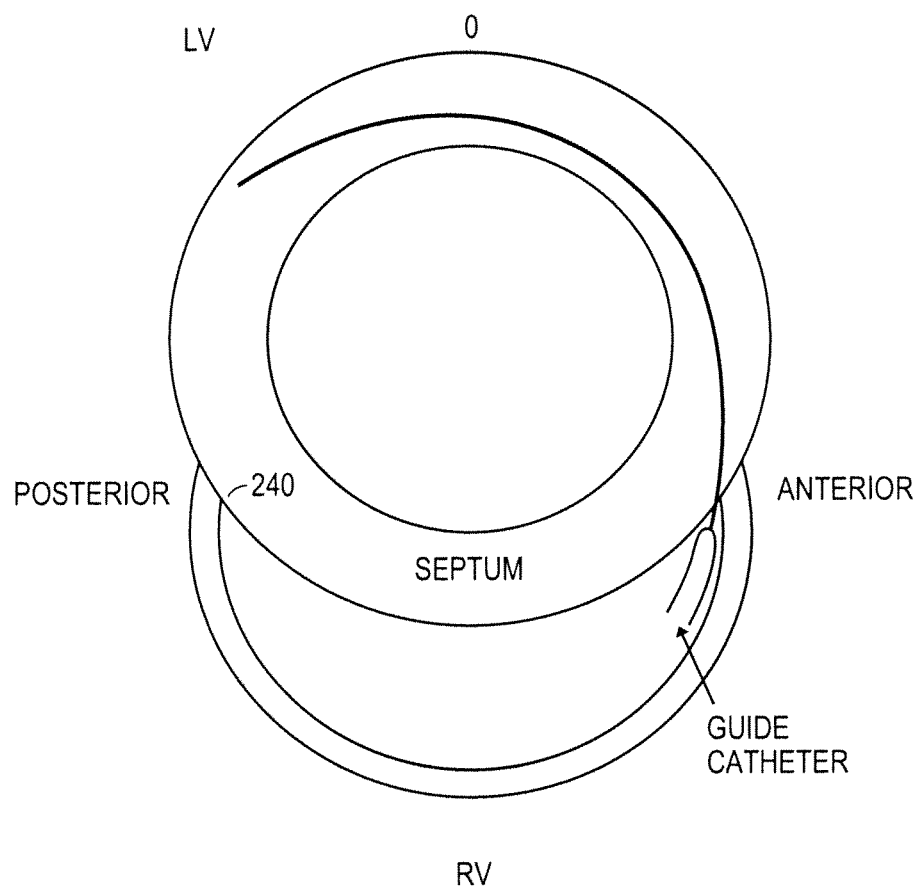
FIG. 2 illustrates an implantable, intramural pacing lead which is introduced along a curved trajectory to simplify introduction.

FIG. 2 illustrates a cross-sectional, planar, short-axis view of the left and right ventricles with the distal end of the guide catheter wedged into the junction of the right ventricular free wall and the interventricular septum. In this example with a simple curve, the pacing lead is advanced well into the left ventricular free wall, well beyond the 0 degree point. Thus with a simple curve, in this case similar to the curvature of the left ventricular epicardial surface, the pacing lead is placed well into the left ventricular free wall.

Numerous methods are available to achieve a curved pacing lead. For example, if the distal portion of the pacing lead is straight, a curved style (inserted along its length can induce a curve in the distal portion of the lead. The curvature of the stylet can be selected to match the corresponding curvature of the heart. Guide wires have been developed with a preferred shape or are steerable. U.S. Pat. No. 5,769,796 issued to Palermo, for example, describes a super-elastic composite guidewire. This is a composite guidewire for use in a catheter and is used for accessing a targeted site in a patient's body. The guidewire core or guidewire section may be of a stainless steel or a high elasticity metal alloy, preferably a nitinol-type of super-elastic alloy, also preferably having specified physical parameters. The composite guidewire assembly is especially useful for accessing peripheral or soft tissue targets. Variations include multi-section guidewire assemblies having, in part, super-elastic distal portions and super-elastic braided reinforcements along the mid or distal sections. U.S. Pat. No. 5,480,382 issued to Hammerslag and U.S. Pat. No. 6,165,139 issued to Damadian, for example, describe steerable guidewires. In certain cases, a movable pull wire extends through the guide wire to its tip. Pulling on this wire causes the tip of the guide wire to bend. Similar approaches can be employed to steer a pacing lead.

Several imaging techniques are available (e.g., X-ray, MRI, echocardiography) to follow or track pacing lead placement. In cardiac catheterization laboratories, for example, X-ray imaging is often used to position catheters within the right ventricular chamber. The same equipment and imaging can be used in the positioning of the pacing lead within the intramural space of the myocardium. For example, once the pacing lead is within the myocardial tissue, the relative circumferential or base-to-apex direction of the guidewire advance can be easily observed. The relative endo-to-epicardial positioning is somewhat more difficult to ascertain, but it can be inferentially or relatively determined in response to the movement of the pacing lead in relationship to the left ventricular cavity.

The positioning of the pacing lead into the left ventricular myocardium can also be guided by echocardiography. Ultrasound imaging, echocardiography, is widely available and provides excellent visualization of cardiac structures. Echocardiographic guidance can facilitate placing the lead. The echo images can help with the positioning of pacing lead within the myocardium. In real time, the echo images provide the exact positioning of these leads within the myocardium. This real time imaging makes placement of these leads easier. Transthoracic and transesophageal echocardiographic views can also be used.

Figure 3A:
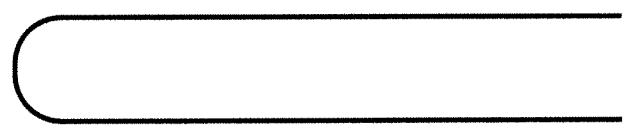
FIGS. 3a-3c illustrate several examples of pacing lead tips which enhance echo-based imaging to facilitate placement.
Figure 3B:
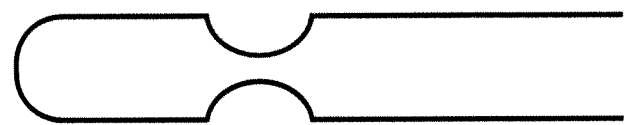
Figure 3C:
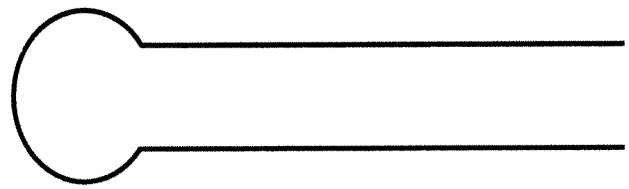

The lead itself is made more visible under echo by having multiple surface features to reflect the echo sound. A simple example of this surface is the commonly used clinical braided or coiled guide wire. One potential difficulty with using echo guidance is to follow the tip of the pacing lead. The rest of the pacing lead must follow the tip, so knowledge of tip position is critical. A two-dimensional echo view takes a thin slice, in effect, across the left ventricle. With this thin slice, the tip of the pacing lead may move out of the field of view, and thus may not be easily recognized. FIG. 3a, for example, depicts a uniformly-shaped tip for a pacing lead. This shaped tip may be hard to follow accurately under echo. Simple variations of this design are depicted in FIGS. 3b-3c, to facilitate tracking. By having a known, different shape at the tip of the pacing lead, the exact position of the tip can be easily followed.

The pacing lead itself can be modified or altered to increases its visualization under echo. As described in U.S. Pat. No. 6,053,870, transverse notches in the lead increase the echo reflecting area, thus enhancing the ultrasound image. As described in U.S. Pat. No. 6,106,473, the lead can be coated with material to enhance its echogenicity. The lead can also generate sound waves as described in U.S. Pat. No. 5,967, 991. A piezo-driver assembly is coupled to the lead, causing the tip to vibrate. These vibrations can be matched to the frequency of the echocardiographic transducer. (Armstrong G, Cardon L, Vilkomerson D, Lipson D, Wong J, Rodriguez L L, Thomas J D, Griffin B P. Localization of needle tip with color doppler during pericardiocentesis: In vitro validation and initial clinical application. J Am Soc Echocardiogr 2001 January; 14(1):29-37).

Figure 4A:
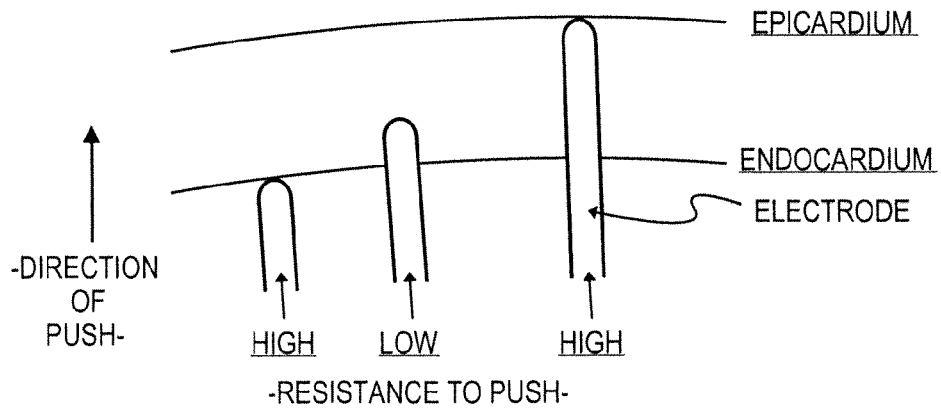
FIG. 4a illustrates the resistance forces associated with the endocardial or epicardial surfaces during lead/electrode introduction.
Figure 4B:
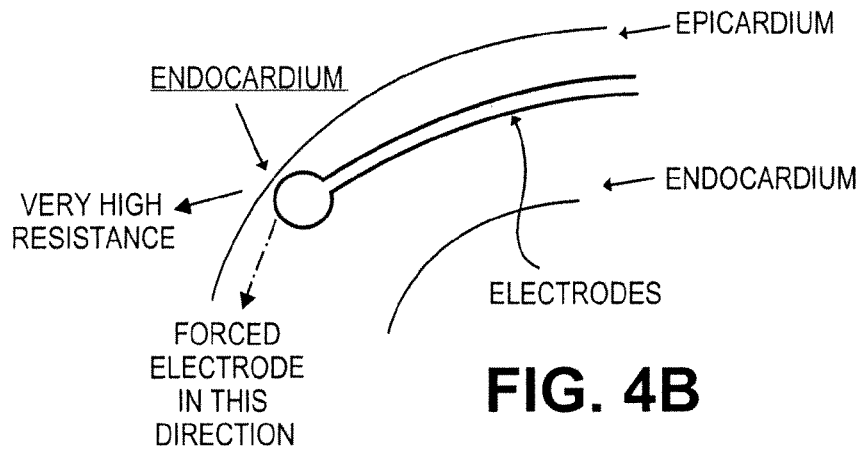
FIG. 4b illustrates an exemplary pacing lead with a spherical shaped tip to enhance echo-based imaging and minimize likelihood of lead introduction inadvertently piercing the epicardial tissue during introduction.
Figure 4C:
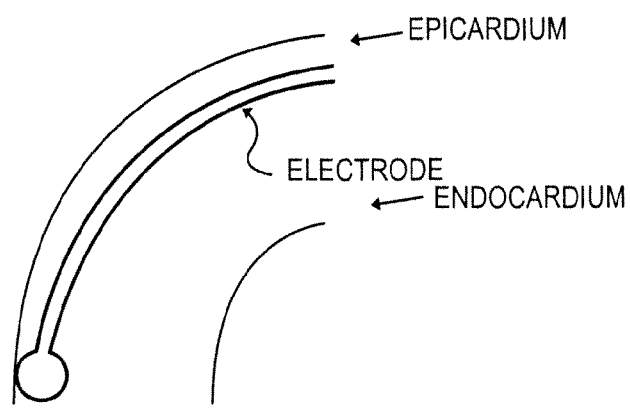
FIG. 4c depicts an exemplary pacing lead having a shaped tip and deflectable shaft to minimize forces exerted against the epicardial surface during lead introduction.

During placement, it is also possible to ascertain the relative position of the pacing lead within the myocardium, based upon the inherent tissue property differences of the intramural space and boundary tissues of the epicardium. The actual resistance to pushing the pacing lead is very different on the surfaces versus the interior of the myocardium, and the tactile feedback of the user will likely suffice to confirm the relative position is being maintained within the intramural space. FIG. 4a illustrates these differences, and it can be appreciated that piercing or exiting the endocardial or epicardial surface requires more force than pushing the pacing lead through the interior myocardium. Consequently, these physical characteristics of the heart can be used to keep the pacing lead within the myocardium. FIG. 4b illustrates a cross-sectional view of the left ventricle, including a pacing lead with a spherical shaped tip introduced into the left ventricular free wall. The tip is being pushed against the epicardial surface. The angle at which the tip is being pushed against the epicardium and the spherical shape of the tip create a very high force, which opposes the pacing lead from being pushed through the epicardium. The force or resistance deflects the tip and keeps the pacing lead within the myocardium as the lead is advanced, as shown in FIG. 4c. The pacing lead thus remains just below the epicardial surface as it is pushed around the left ventricular free wall.

Adjusting the strength or stiffness of the pacing lead can also assist this restraining force. To accomplish this purpose, the ideal lead would incorporates two extreme functions, namely, being relatively stiff to provide column strength along its length for pushing the lead into the myocardial tissue, while offering a relatively flexible or floppy distal segment to avoid trauma to the epicardial surface and provide the desired steering characteristics. By selecting the appropriate balance of structural features and flexibility, the pacing lead can be advanced into the myocardium with relatively modest prospect of inadvertently exiting through the epicardium or endocardium. The pacing leads will thus preferably have variable flexibility along the length of the lead. U.S. Pat. No. 6,146,339 issued to Biagtan, for example, describes a guide wire with operator controllable tip stiffness. Many different approaches are available to vary the stiffness of the pacing leads. For example, U.S. Pat. No. 5,957,903 issued to Mirzaee describes a guidewire whose stiffness is adjusted by advancing or retracting a movable core within the guidewire.

Figures 5A, 5B, 5C, 5D:
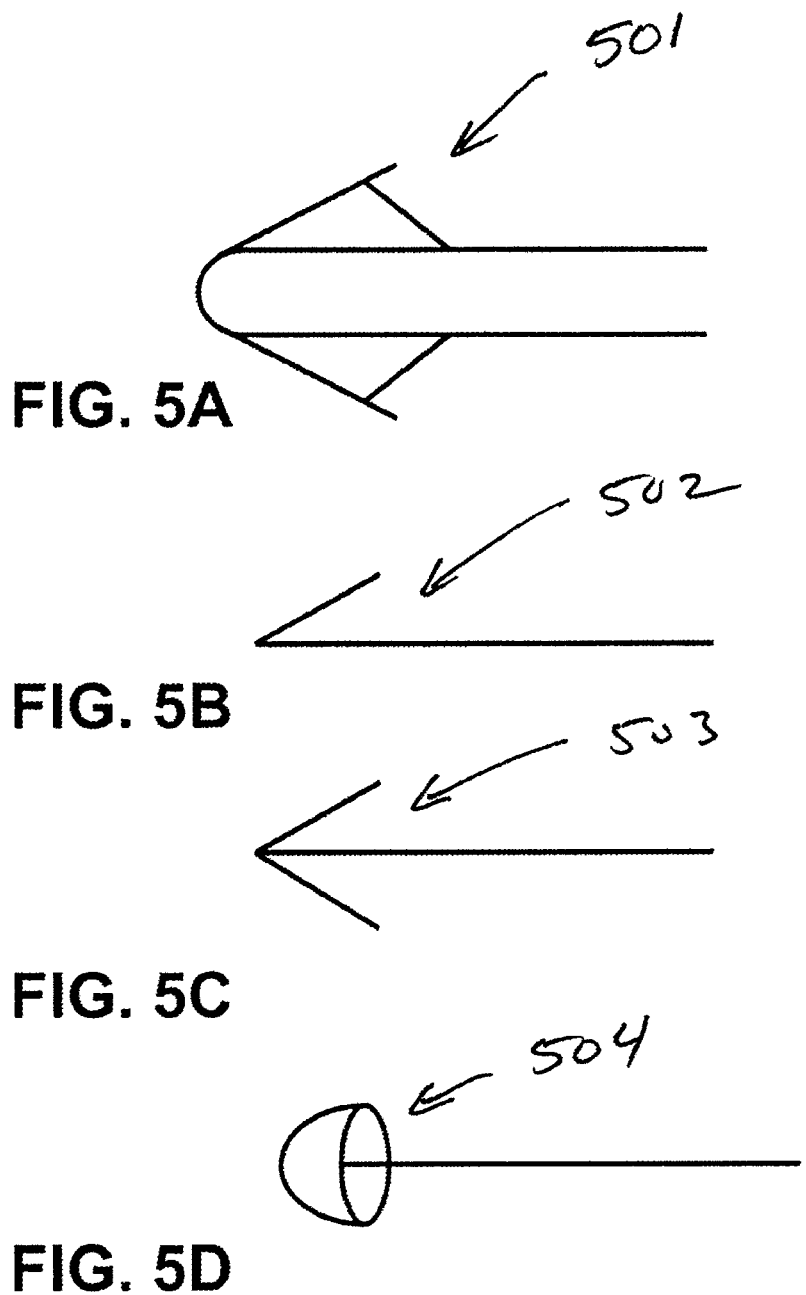
FIGS. 5a-5d illustrate several exemplary anchoring elements for the intramural pacing lead/electrode system.

The anchoring element comprises another important component of the lead system. Once the pacing lead is properly positioned, the anchoring element is deployed to maintain the pacing lead in this position. FIGS. 5a-5d illustrate several exemplary anchoring elements 501, 502, 503, 504 for the intramural pacing lead/electrode system. FIG. 5d, for example, provides an anchoring element 504 serving dual functions, namely, preventing the pacing lead from exiting the epicardium and keeping the lead in its proper position within the intramural space of the myocardium.

Figure 6A:
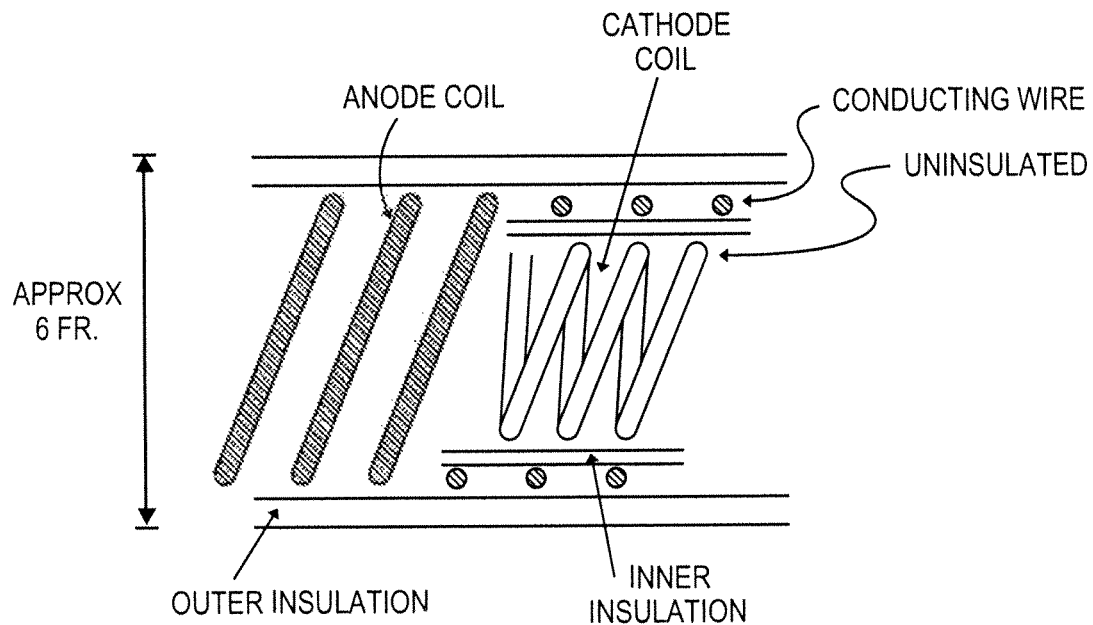
FIG. 6a illustrates shaft designs for the intramural lead/electrode systems.
Figure 6B:
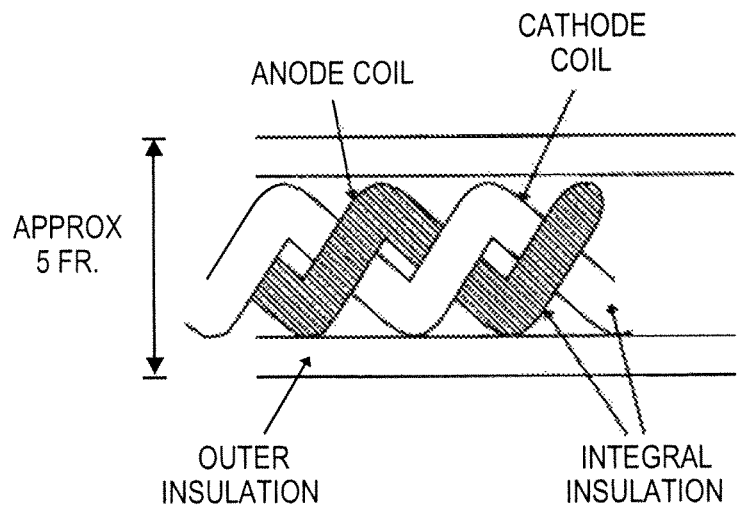
FIG. 6b illustrates an exemplary, reduced-profile lead design.

FIGS. 6a and 6b illustrate alternative body designs for the leads. FIG. 6a depicts a traditional design for a bipolar lead. An electrical insulator separates two conductors, and both conductors are enclosed within an outer insulator. The conducting wire is not insulated. FIG. 6b depicts shows a design where both conducting wires are insulated and enclosed within an outer insulator, which offers a reduced profile design. As described above, however, these standard designs may be less suitable for the right ventricular placement of the left ventricular pacing lead, since their relatively smooth surfaces will not likely image well under echo techniques. Without distinctive features, it is believed that the distal end of the lead would be hard to follow during placement with echo guidance. More importantly, the stiffness characteristics of these standard leads are not suitable to provide the column strength necessary to advance the leads through myocardial tissues. As these leads are pushed through the tissue, resistance to further insertion increases until one portion of the lead buckles. At this point, the lead cannot be further advanced. Since these traditional leads are not currently designed for applications of this type, modifications are believed necessary to minimize tissue irritation and the build-up of scar tissue by the electrodes.

Figure 6C:
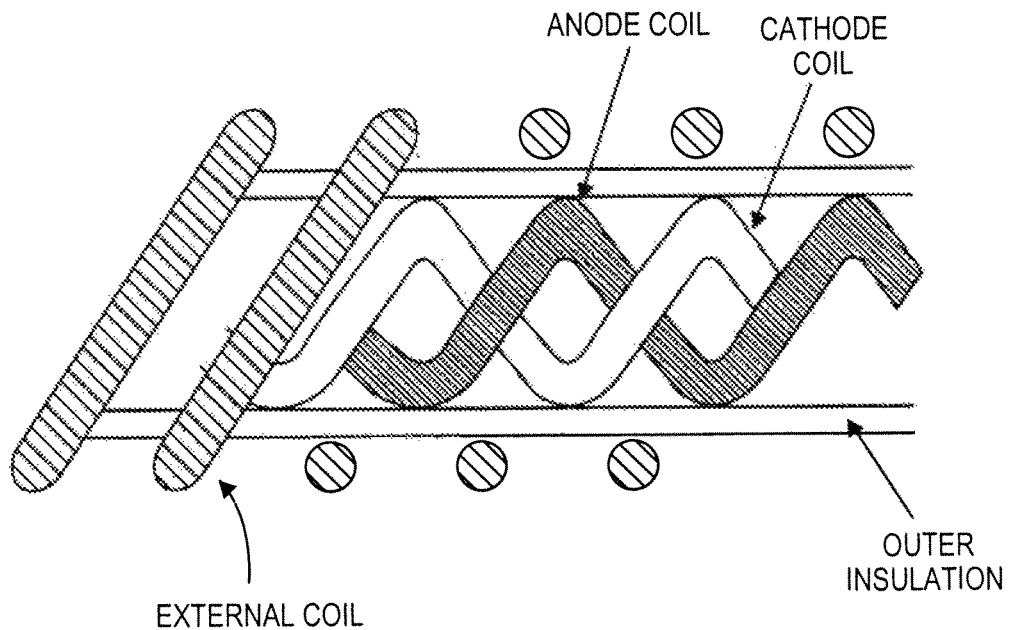
FIG. 6c illustrates an exemplary design providing for an external coiled wire around the intramural lead.
Figure 6D:
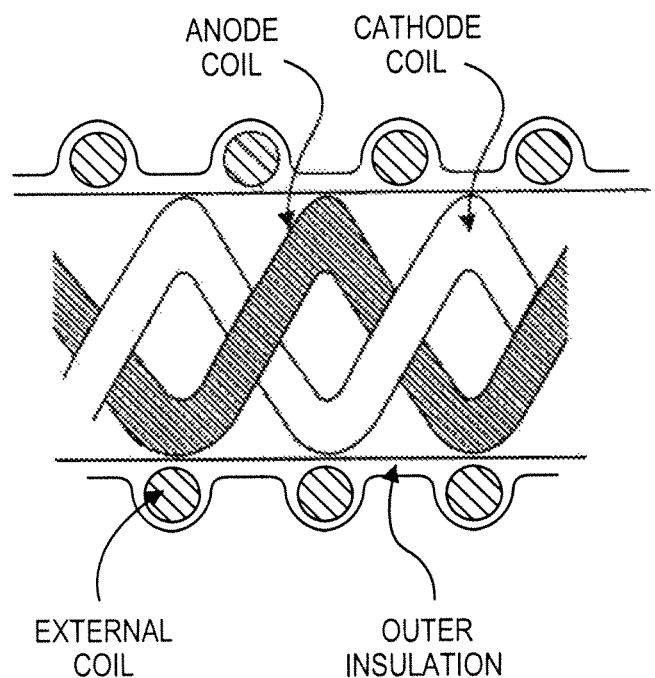
FIG. 6d illustrates an external coiled wire incorporated into the outer insulator of an exemplary intramural lead.

Therefore, a new lead design is required for the right ventricular introduction and placement of the left ventricular lead within the intramural space of the myocardium. As described in U.S. Pat. No. 6,106,473, the outer insulator of the lead is coated with material to enhance its tracking characteristics and echogenicity. FIGS. 6c and 6d show additional surface features to increase the echogenicity of the lead. In FIG. 6c, an external coiled wire is wrapped around the lead, which provides a lead that is more visible under echo (by having an echogenic coating and including multiple surface features to reflect the echo sound). In FIG. 6d, an external coiled wire is incorporated into the outer insulator of the lead. The outer insulator of the lead is coated with material to enhance its echogenicity. This lead is more visible under echo by having the multiple surface features to reflect the echo sound and by the surface coating.

Figure 7:
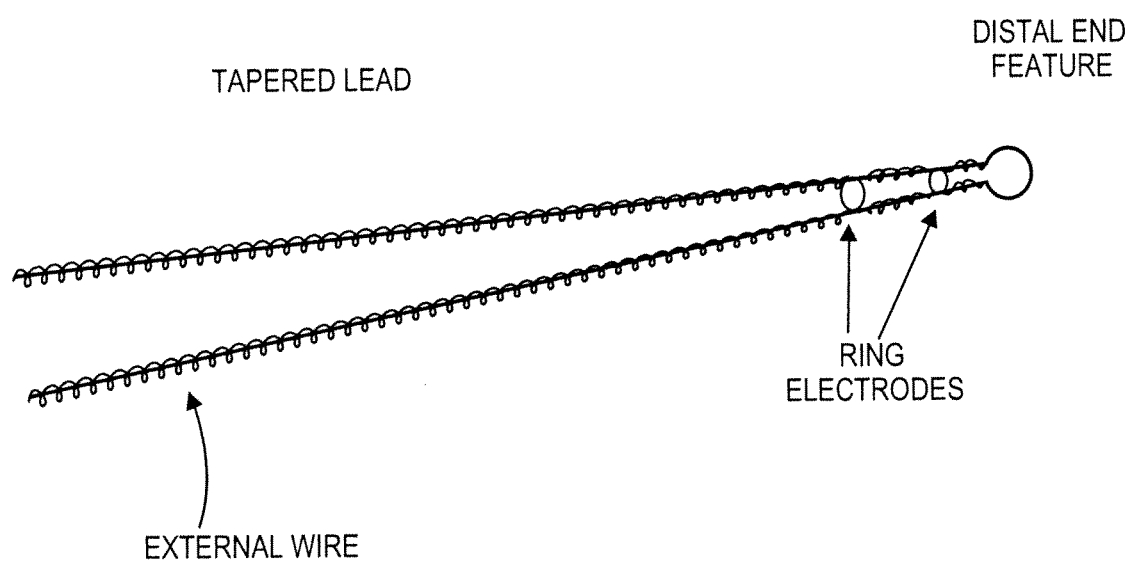
FIG. 7 illustrates exemplary designs for a tapered pacing lead, including a distal feature to provide enhanced echo-based imaging and tracking.

In connection to the leads described in FIGS. 6c and 6d, FIG. 7 illustrates a relatively extended distal section of the lead. The distal end of the lead has a distinctive feature, which facilitates echo tracking. In this example, the tip has a spherical shape. This shape can be solid or a wire mess to reduce tissue trauma. In other designs, additional imaging-enhancing features can be employed, including the ring electrode itself. Since the smooth metal surface of the electrode may offer reduced echo visibility, a contrast can be incorporated in the design which better distinguishes the echogenic wire wrap part of the lead versus the echolucent electrode associated with the tip of the lead.

By selecting the appropriate lead strength or stiffness, the lead is able to be easily introduced into the intramural space, while posing a reduced likelihood of inadvertently piercing epicardial or endocardial surfaces. As shown in FIG. 7, for example, the thickness and relative stiffness of the leads desirably varies along the length of the electrode to support steering through the myocardial tissue and provide conformity with the curved, ventricular free walls. The flexibility of the tip minimizes long-term trauma with the surrounding tissue, resulting in decreased scar formation by the electrodes, and thus providing better long-term electrical pacing characteristics.

Other components of the pacing leads are constructed by standard techniques known to those familiar with the arts. Numerous materials, such as platinum or tantalum coated MP35N alloy wire, can be used for the conductor. At the distal end, the conductor makes electrical contact with the tissue via an electrode, commonly a ring electrode. The electrode can elude an anti-inflammatory cortico-steroid such as sodium dexamethasone to reduce irritation of tissue adjacent to the electrode. Insulation materials such as polyurethane, silicone, and ethylene tetra fluorethylenefluoropolymer are used. The proximal end is directly connected to the pacemaker through an IS-1 standard connector with a sealing-ring.

In addition to the use of the above-described use of the present invention for support of cardiac resynchronization therapies, further adaptations of the present invention are contemplated for management of other electrical stimulation therapies of heart tissue, such as cardiac contractility modulating signals. Prolonging membrane depolarization by voltage-clamp techniques applied to isolated cardiac muscle increases trans-sarcolemmal calcium entry into the cell and thus enhance contractility (Wood E H, Heppner R L, Weidmann S. Inotropic effects of electric currents. I. Positive and negative effects of constant electric currents or current pulses applied during cardiac action potentials. II. Hypotheses: calcium movements, excitation-contraction coupling and inotropic effects. Circulation Research 1969; 24:409-445.). Extracellularly applied electrical signals have a similar effect as voltage clamping in muscles isolated from normal animals and failing human hearts. When applied regionally, electrical currents enhance contractility of normal and failing hearts in-vivo (Mohrl S, He K L, Dickstein M, Mika Y, Shimizu J, Shemer I, Yi G H, Wang J, Ben-Haim S, Burkhoff D. Cardiac contractility modulation by electric currents applied during the refractory period. American Journal of Physiology 2002; 282:H1642-H1647.).

While this concept of altering regional contractility has many potential advantages, there are currently several limitations presented when considering traditional leads and electrode placement techniques. If the leads use ring-type electrodes, for example, the leads are in-effect only point sources of the current, and only small regions of the myocardial will experience the positive contractility effects. Better results could be obtained by creating a larger electrical field, which generally requires an electrode with a longer length. In addition to the electrodes themselves, placement can be a problem. For most patients, however, left ventricular dysfunction or failure is the main problem. Thus, the leads need to be positioned within the left ventricle. A catheter-based introduction approach (i.e., an intracardiac lead introduced from the left ventricular cavity into the adjacent, wall) can deliver these pacing electrode leads within the left ventricular cavity, which is believed to present a huge risk for thrombus formations and embolic clots. For external placement, a thoracotomy is required.

Figure 8:
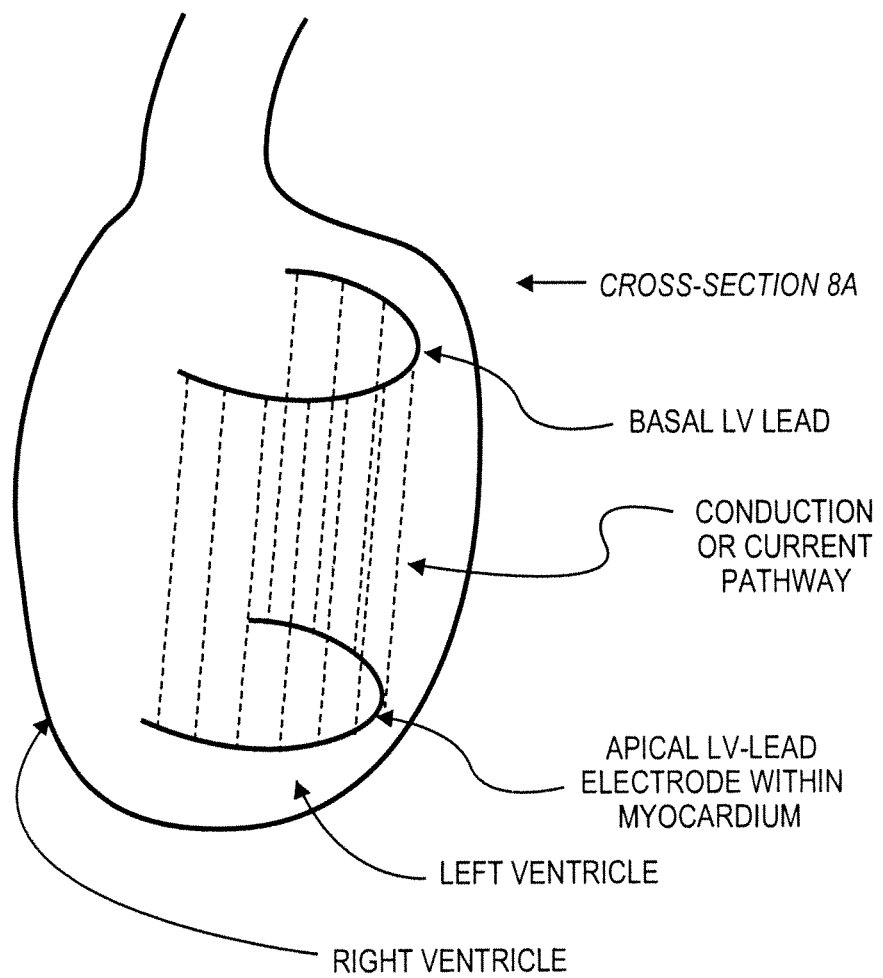
FIG. 8 depicts two pacing leads, placed circumferentially and spaced-apart vertically, to enable a uniform current distribution throughout the myocardium.
Figure 8:
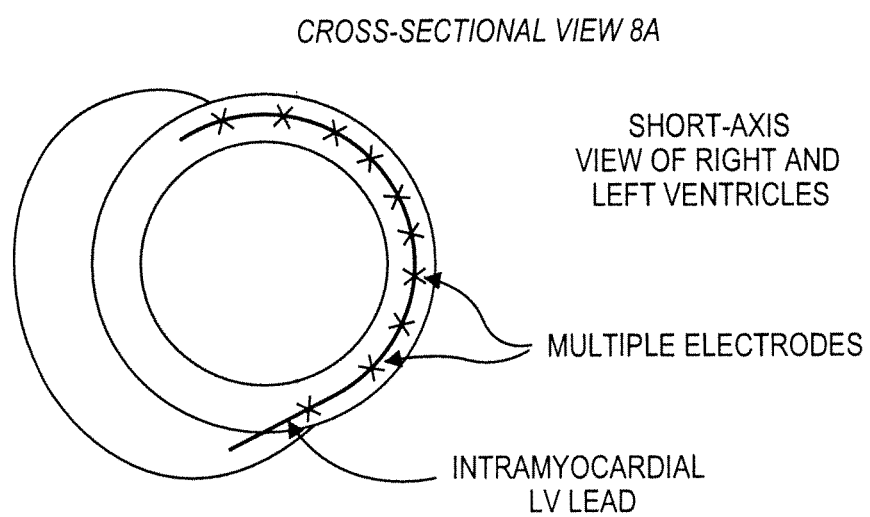

The same approaches described above can be employed to place leads in the left ventricular free wall or septum via a catheter and without touching the left ventricular endocardial surface. FIG. 8 shows a view of the left ventricular free wall. Embedded within the left ventricular myocardium are two pacing leads, which are placed circumferentially, as previously described. In this illustration, one lead is placed closer to the base, while the other lead is placed closer the left ventricular apex. The leads have either continuous or intermittent connection to the myocardium. In this example, the leads are placed around the entire left ventricular free wall. Partial coverage of the left ventricular free wall is also possible. By covering a broad area, the leads enable a uniform current distribution over a larger portion of the left ventricle. The leads may optionally include intramural, myocardial electrode implants that align with identified areas of myocardial tissue requiring resynchronization or adjunctive pacing.

Ventricular fibrillation, chaotic electrical activity of the ventricular myocardium, is a life-threatening event, if not treated quickly. Implantable defibrillators sense the heart's electrical activity and defibrillate the heart when needed. Since the initial concept, the size and functionality of the implantable defibrillators have improved. Two defibrillator issues still need to be resolved, namely, the size of the defibrillators and the generated electrical field for defibrillation. While these issues may seem different, the issues are tied together. The magnitude of the energy required to successfully defibrillate the heart with a safety margin is a primary determinant of the implantable defibrillators size. The leads used to distribute the defibrillation shock determine, in part, how much current will be needed.

Initially, pacing leads were placed external to the heart. Modern pacing systems favor intracardiac leads, which are often transvascular, venous implants. In one approach, the lead is placed in the right ventricle adjacent the endocardium, and the defibrillator itself constitutes the other lead electrode. The stimulator or pacing current is spread between these two leads, such that it flows from the right ventricular lead to the implantable defibrillator, which is often located in the pectoral region. A disadvantage of this approach is the low current density delivered to the left ventricular apical region. Another approach, shown in U.S. Pat. No. 6,370,427 uses leads in both the left and right ventricular chambers. The shock current can be distributed between the right and left ventricular leads or between the leads and the implantable defibrillator. Unfortunately, this approach fails to provide an even current distribution, and also presents additional concerns relating to potential lead thrombogenicity when placed directly within the left ventricular cavity.

Figure 9A:
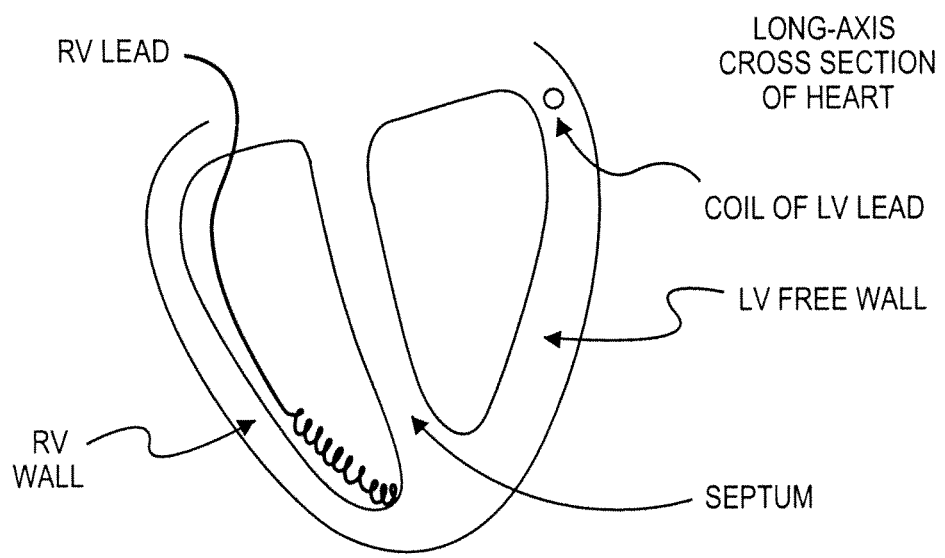
FIGS. 9a and 9b depict placement of a coil electrode segment of the left ventricular lead located in the lateral wall close to the base of the heart, and a coil electrode segment of the right ventricular lead placed by the apex of the heart.
Figure 9B:
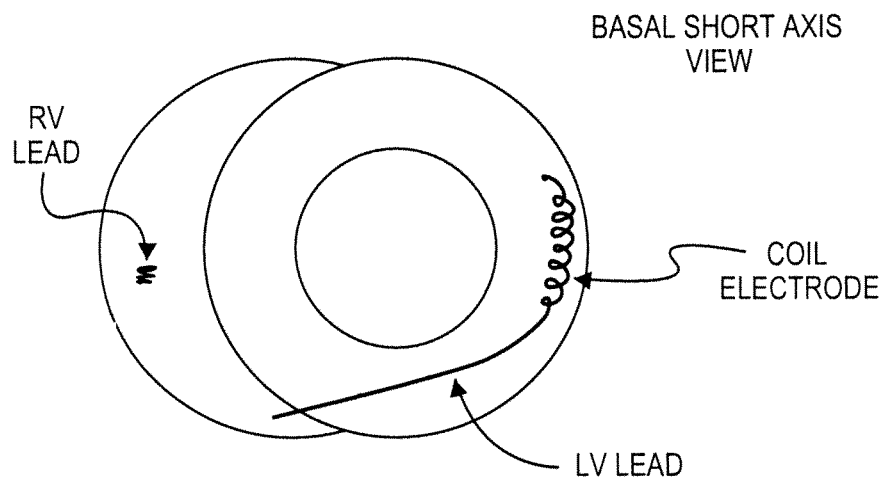

By placing a lead within the left ventricular lateral wall close to the base of the left ventricle, and positioning the other lead in the apical right ventricle, a better current distribution can be achieved. In this example, both ventricular regions will receive appropriate cardioversion and defibrillator shock. FIGS. 9a and 9b, for example, show desired lead positions. The coil electrode segment of the left ventricular lead is placed in the lateral wall close to the base. Placing the left ventricular lead within the myocardium further reduces the magnitude of current needed to successfully defibrillate the heart. The coil electrode segment of the right ventricular lead is desirably placed within the right ventricular cavity by the apex. As described above, the left ventricular lead is positioned just below the epicardial surface. This placement of the left and right ventricular leads provides an improved and more predictable current distribution across both ventricles.

Figure 10:
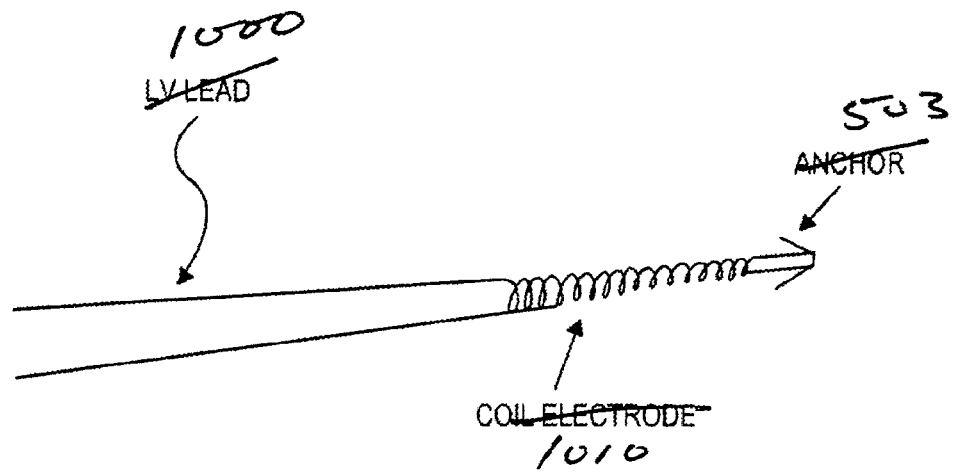
FIG. 10 illustrates one possible configuration for the left ventricular lead.

This left ventricular lead can be placed from the right ventricle as described for the resynchronization therapy, and can be used in combination with resynchronization therapy in an adjunctive manner. FIG. 10 shows one possible configuration for the lead 1000 within the left ventricular myocardium. By selecting the appropriate lead strength or stiffness, the lead can be advanced into the myocardium with little chance of exiting through the epicardium or endocardium. The thickness and stiffness characteristics of the leads preferably vary along the length of the electrode. The flexibility of the tip prevents the lead from penetrating the epicardium or the endocardium. The flexible tip also minimizes long-term trauma with the surrounding tissues, and tends to decrease scar formation by the electrodes, thereby ensuring better long-term electrical characteristics. The stiffer body component of the proximal portion of the lead enhances introduction into the myocardium.

The coil-shaped electrode 1010 can be made from a single wire, but multi-filament wire is preferred. The coil-shape provides a large surface area to reduce electrical resistance, and more effectively distributes current density along the desired myocardial regions of the heart. Platinum clad titanium, platinum clad tantalum, or platinum coated MP35N wire can be used for the coil. The coil-shaped electrode portion of the lead makes the distal end of the lead echogenic, thus making echo tracking during positioning easier. The electrode is connected to a coil conductor, which carries the current from the connector pin to the electrode. Insulation materials such as polyurethane, silicone, and ethylene tetrafluor ethylenefluoropolymer can be used along the length of the lead. A conventional connector pin is used to attach the lead to the implantable defibrillator.

It is also recognized that the above-described technique for lead introduction can be practiced to introduce discreet, implantable devices within the myocardial wall to provide acute reinforcement of localized ventricular regions damaged by a recent myocardial infarction. These reinforcement devices can be placed into the anterior and posterior left ventricular wall, as well as the septum from a right ventricle, using the approaches described in this application for placement of LV pacing leads and intramural pacing electrodes. Again, the steerable catheter is placed into the right ventricle rather than the left ventricle. The catheter is positioned against the septum and the guidewire is advanced into the septum as far as desired into the left ventricular free wall. The remaining deployment of these reinforcement devices follows the same steps as generally described above.

Figure 11:
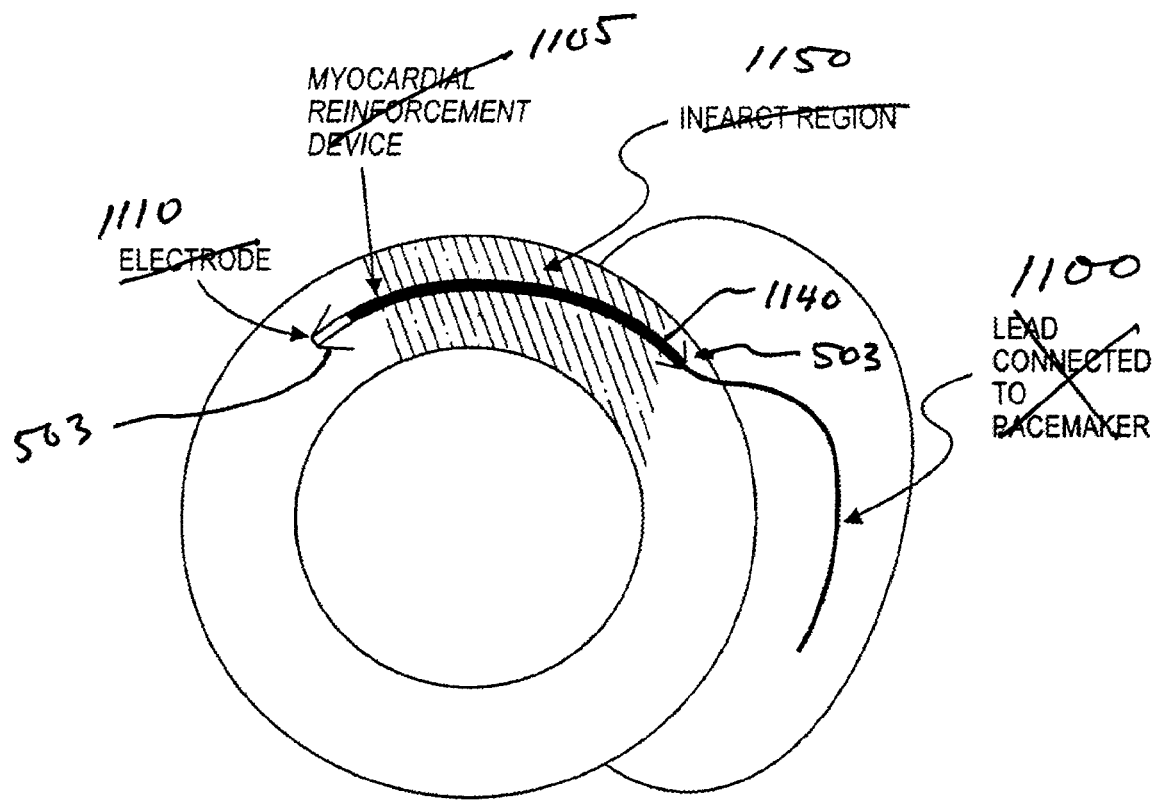
FIG. 11 depicts an exemplary myocardial reinforcement device implanted within an anterior wall infarct with the proximal end of the device connected to a lead.

As shown in FIG. 11, the intramural reinforcement 1105 can also be used as an electrical bridge across the infarct region. In this example, the implantable device is placed across an anterior wall infarct 1150. The electrode 1110 of the MyoMend device embedded in the normal lateral wall is in electrical contact with the surrounding tissue. The body of the device is encapsulated with an insulator 1140. The other end of the device is connected to a lead 1100, which in turn connects to a pacemaker. If electrical synchronization therapy is needed, the left ventricular lateral wall can be stimulated through the lead/electrode system.

It is also recognized that the above-described technique for introducing intramural pacing leads could be accomplished with the combination of two devices. A novel intramural guidewire and a separate intramural pacing lead can be used. The guidewire would possess the features described above and would be optimized for intramural navigation. The guidewire would include all of the novel features for pacing and intramural anchoring described in sections above. The guidewire would be introduced to the target intramural tissue first and the pacing lead would be introduced second. The pacing lead and/or guidewire could be of a solid or hollow design.

It is also recognized that a device similar to that shown in FIG. 11 could be fabricated that would be an electro-active bridge. The device would be placed across the infarct region in a manner described above. The device would use the heart's systole deformation to store strain energy and then convert this energy into electrical energy to be discharged back to the distal end of the device at the next systolic cycle. This discharge would allow depolarization to spread to the opposite side of the infarct region that would otherwise be blocked. The device could also have an electrical sensing circuit/system and logic within to better time the exact point of discharge.

Other embodiments of the invention will be apparent to those of skill in the art from consideration of the specification and practice of the inventions disclosed herein. It is intended that the specification and examples be considered as exemplary only.

What is claimed is:

1. A method for direct localized therapeutic treatment of myocardial tissue having a pathological condition comprising the steps of:
   a. identifying a target region of the myocardial tissue having an epicardial region and an endocardial region and an intramural space defined between, said target region including a myocardial infarct or ischemic zone;
   b. delivering a lead having an electrode to said intramural space, the lead including a first end and a second end and an insulator along a portion of its length; and
   c. implanting said electrode in normal tissue distal of said myocardial infarct or ischemic zone relative to said first end; and
   d. implanting at least a portion of said lead such that said implanted portion crosses through said myocardial infarct or ischemic zone of said target region within said intramural space so as to physically modify the mechanical properties of at least a portion of the myocardial tissue of the target region substantially identified in step (a), at least a portion of the insulator being in said myocardial infarct or ischemic zone,
   wherein said lead is configured to be connected to a therapeutic or diagnostic device.

2. The method of claim 1 wherein the modified mechanical properties include an increase in systolic performance.

3. The method of claim 2 wherein the modified mechanical properties further include substantially no decrease in diastolic performance.

4. The method of claim 1, wherein the lead includes an electro active bridge for spanning said infarct or ischemic zone.

5. The method of claim 1, wherein said delivering step further comprises delivering a substantially arcuately curved lead into the intramural space.

6. The method of claim 5 wherein said delivering step further comprises using a stylet to deliver said lead to said intramural space.

7. The method of claim 5 wherein said delivering step further comprises using a guidewire to deliver said lead to said intramural space.

8. The method of claim 1, wherein said lead further comprises echo features for aiding visualization.

9. The method of claim 1, wherein said lead further comprises radiopaque features.

10. The method of claim 1, wherein said lead further comprises a drug eluting surface.

11. The method of claim 1, further comprising connecting said lead to a therapeutic or diagnostic device.

12. The method of claim 11, wherein the lead further includes an anchor, said implanting step further comprising:
   implanting said anchor in normal tissue proximal of said myocardial infarct or ischemic zone relative to said first end of the lead, said anchor being connectable to the therapeutic or diagnostic device.

13. The method of claim 12, wherein the insulator extends intramurally completely across said myocardial infarct or ischemic zone.

14. The method of claim 11 wherein the therapeutic or diagnostic device is a pacemaker.

15. The method of claim 11 wherein the therapeutic or diagnostic device is a cardioverter/defibrillator.

16. The method of claim 11 wherein the therapeutic or diagnostic device is a cardiac resynchronization device.

17. A method for direct localized therapeutic treatment of myocardial tissue having a pathological condition comprising the steps of:
   identifying a target region of the myocardial tissue having an epicardial region and an endocardial region and an intramural space defined between, said target region including a myocardial infarct or ischemic zone;
   delivering an intramural reinforcement having an electrode to said intramural space, said intramural reinforcement including a first end and a second end and an insulator along a portion of the length of the intramural reinforcement, said intramural reinforcement being configured to be connected to a therapeutic or diagnostic device; and
   implanting an electrode in normal tissue distal of said myocardial infarct or ischemic zone relative to said first end;
   implanting at least a portion of said intramural reinforcement such that said implanted portion crosses through said myocardial infarct or ischemic zone of said target region within said intramural space so as to physically modify the mechanical properties of at least a portion of the myocardial tissue of the target region substantially identified in the indentifying step, at least a portion of the insulator in said myocardial infarct or ischemic zone.

18. The method of claim 17, further comprising connecting a therapeutic or diagnostic device to the intramural reinforcement, the therapeutic or diagnostic device comprising one of a pacemaker, a cardioverter/defibrillator, and a cardiac resynchronization device.

19. The method of claim 17, wherein the intramural reinforcement includes an electro active bridge for spanning said infarct or ischemic zone.

20. The method of claim 17, wherein said delivering step further comprises delivering a substantially arcuately curved intramural reinforcement into the intramural space.

21. The method of claim 17, wherein said delivering step further comprises using at least one of a stylet and a guidewire to deliver said intramural reinforcement to said intramural space.

22. The method of claim 17, wherein said intramural reinforcement further includes at least one of echo features for aiding visualization, radiopaque features, and a drug eluting surface.

23. The method of claim 17, wherein the intramural reinforcement further includes a first anchor distal of the insulator and a second anchor, said implanting step further comprising:

implanting said first anchor in normal tissue distal of said myocardial infarct or ischemic zone relative to said first end of the intramural reinforcement; and implanting said second anchor in normal tissue proximal of said myocardial infarct or ischemic zone, said anchor being connectable to the therapeutic or diagnostic device.

24. The method of claim 23, wherein the insulator extends intramurally completely across said myocardial infarct or ischemic zone.

* * * * *